US009615903B2

(12) United States Patent
Green et al.

(10) Patent No.: US 9,615,903 B2
(45) Date of Patent: Apr. 11, 2017

(54) NON-SURGICAL EMBRYO TRANSFER METHOD AND APPARATUS

(75) Inventors: Michael A. Green, Lexington, KY (US); Brett Thomas Spear, Lexington, KY (US)

(73) Assignee: ParaTechs Corp., Lexington, KY (US)

( * ) Notice: Subject to any disclaimer, the term of this patent is extended or adjusted under 35 U.S.C. 154(b) by 1004 days.

(21) Appl. No.: 12/454,805

(22) Filed: May 22, 2009

(65) Prior Publication Data

US 2009/0292162 A1 Nov. 26, 2009

Related U.S. Application Data

(60) Provisional application No. 61/128,726, filed on May 23, 2008.

(51) Int. Cl.
A61D 19/04 (2006.01)
A61B 17/43 (2006.01)
A61B 17/435 (2006.01)

(52) U.S. Cl.
CPC .............. *A61D 19/04* (2013.01); *A61B 17/43* (2013.01); *A61B 17/435* (2013.01)

(58) Field of Classification Search
None
See application file for complete search history.

(56) References Cited

U.S. PATENT DOCUMENTS

| 5,916,144 | A |   | 6/1999 | Li |
|---|---|---|---|---|
| 6,027,443 | A | * | 2/2000 | Nag ................................ 600/33 |
| 6,071,231 | A |   | 6/2000 | Mendoza |
| 6,165,165 | A | * | 12/2000 | Cecchi et al. ................ 604/523 |
| 2003/0208101 | A1 |   | 11/2003 | Cecchi |
| 2003/0216610 | A1 |   | 11/2003 | Kaneko |
| 2004/0261799 | A1 |   | 12/2004 | Mock |

FOREIGN PATENT DOCUMENTS

| FR | 2789292 | 11/2000 |
|---|---|---|
| GB | 2118840 | 11/1983 |
| GB | 2263642 | 4/1993 |

OTHER PUBLICATIONS

Marsk et al. A Simple Method for Non-Surgical Blastocyst Transfer in Mice. Journal of Reproductive Fertilization 1974, vol. 37, pp. 393-398.*

(Continued)

*Primary Examiner* — Louise W Humphrey
*Assistant Examiner* — Charles Zoltan Constantine
(74) *Attorney, Agent, or Firm* — Stockwell & Smedley, PSC

(57) ABSTRACT

A device having a catheter and a hub which facilitates the transfer of an embryo containing solution into the uterus of a mammal, for example, a small mammal such as a rat or mouse. The catheter's shape and tip is designed to simplify insertion and minimize injury to the mammal. The hub is designed to further control the insertion of the catheter and to interface with a pipette, for example, that provides the force required for the transfer of an embryo containing solution. As a result, the transfer can occur without requiring surgery.

25 Claims, 3 Drawing Sheets

(56) References Cited

OTHER PUBLICATIONS

Zheng Zhang, et al., Success of Murine Embryo Transfer Increased by a Modified Transfer Pipette, Journal of Reproduction and Development, vol. 55, No. 1, 2009, pp. 94-94, Society of Animal Reproduction, Japan.
Tammy Davis, Transfer of Mouse Embryos, Bios, vol. 52, No. 3, Sep. 1981, pp. 127-133, Beta Beta Beta Biological Society, U.S.
Terry L. Moler, et al., A Simple Technique for Nonsurgical Embryo Transfer in Mice, Laboratory Animal Science, vol. 29, No. 3, Jun. 1979, pp. 353-356, American Association for Laboratory Animal Science, Memphis, TN.
Hsian-Jean Chin and Chi-Kuang Leo Wang, Utero-Tubal Transfer of Mouse Embryos, Genesis, vol. 30, Issue 2, Jun. 2001, pp. 77-81, Wiley-Liss, Inc.
International Search Report (ISR) and Written Opinion for PCT/US09/03177.
Examination Report for UK Patent Application No. GB1019548.5.
Examination Report for German Patent Application No. 11 2009 001 263.9.

\* cited by examiner

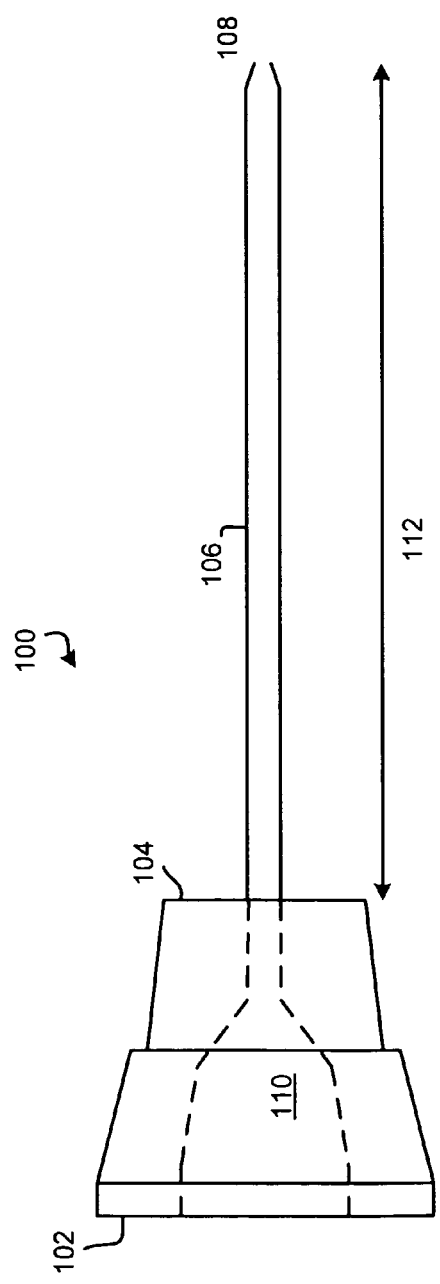
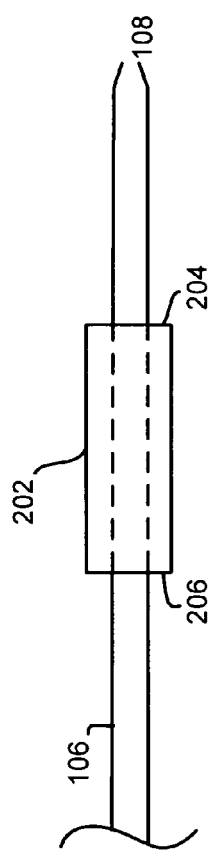
FIG. 1
FIG. 2

NON-SURGICAL EMBRYO TRANSFER METHOD AND APPARATUS

RELATED APPLICATIONS

This application claims priority to U.S. Application Ser. No. 61/128,726 filed May 23, 2008 the disclosure of which is incorporated herein by reference in its entirety.

BACKGROUND OF THE INVENTION

Field of the Invention

The present invention relates generally to embryo transfer techniques and more particularly with a device and method for accomplishing such a transfer without surgery.

Description of Related Art

Existing methods in rodent reproductive sciences have a number of shortcomings that make them expensive, difficult, and inefficient. It generally takes about 30 minutes to transfer embryos to female mice using surgical procedures, although this will vary depending on the expertise of the person performing the technique. Also, surgical embryo transfer involves anesthesia, post-operative care, the use of analgesics, and possible complications including infection. The significance of these issues continues to grow as regulations regarding the use and care of experimental animals expand. Anesthetics and analgesics are relatively expensive as well and some are considered controlled substances, so the elimination of these reagents represents a considerable cost savings and reduction of regulations.

Furthermore, the technical expertise required for surgical transfer of embryos is considerably significant and, thus, limits the number of potential users of genetically modified mice.

Thus, there remains the need for devices and methodology that eliminates the need for anesthesia, surgery, and the use of analgesics, and dramatically reduces the time needed for post-operative care and essentially eliminates infection and other post-operative complications. Also a reduction in the technical expertise required for surgical transfer of embryos would help expand the number of potential users of genetically modified mice and other animals.

BRIEF SUMMARY OF THE INVENTION

Embodiments of the present invention relate to a device, and a method for its use, having a catheter and a hub which facilitates the transfer of an embryo containing solution into the uterus of a mammal, for example, a small mammal such as a rat or mouse. The catheter's shape and tip is designed to simplify insertion and minimize injury to the mammal. The hub is designed to further control the insertion of the catheter and to interface with a pipeter, for example, that provides the force required for the transfer of an embryo containing solution. As a result, the transfer can occur without requiring surgery.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF DRAWINGS

Various aspects of a non surgical embryo transfer device are illustrated by way of example, and not by way of limitation, in the accompanying drawings, wherein:

FIG. 1 depicts a non-surgical embryo transfer device in accordance with the principles of the present invention.

FIG. 2 depicts the device of FIG. 1 in addition to a speculum.

DETAILED DESCRIPTION OF INVENTION

Figure 3:
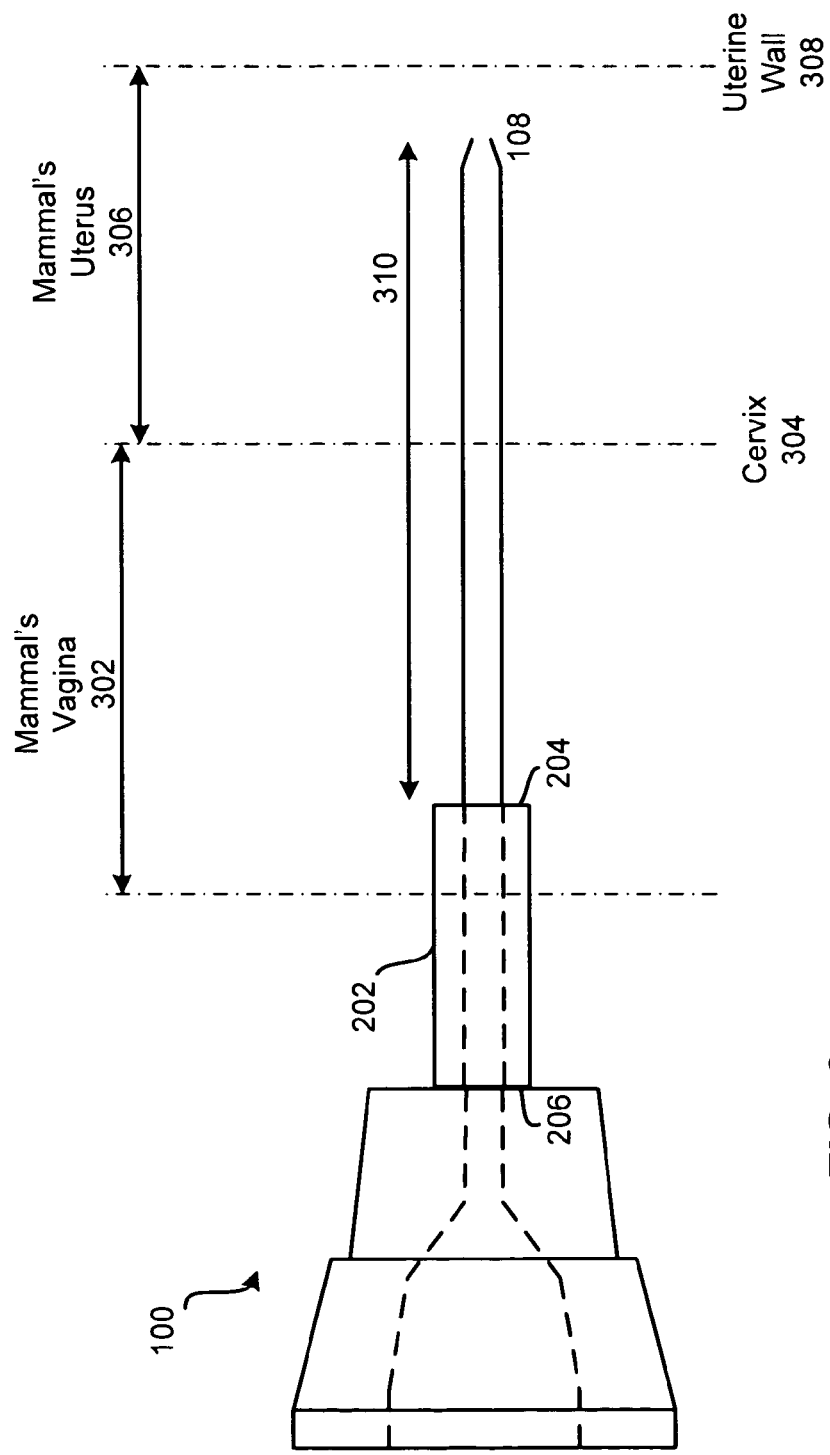
FIG. 3 depicts the device of FIG. 1 in relation to insertion in an animal in accordance with the principles of the present invention.

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

Embodiments of the present invention relate to intrauterine transfer of embryos in animals, for example in animals such as small rodents, including but not limited to mice and rats. Other animals in addition to rodents are contemplated within the scope of the present invention as well.

A small, flexible plastic device has been developed to physically introduce a catheter through the cervix of the small rodent, which can then be used to transfer a solution containing embryos into the uterus. Once transferred, the embryos attach to the endometrial tissue, implant and develop.

This device has a number of beneficial characteristics that make it well-suited to traverse the cervix without damaging the cervical or uterine tissue. For example, the length of the device is designed, such that it is long enough to get past the cervix but not too long to damage endometrial tissue, this allows the tip to be located within the uterus at a position which improves the likelihood of successful embryo transfer. Also, in at least one embodiment, the hub interacts with a separate speculum to further assist with correctly positioning the device in a female rodent, or animal, for embryo transfer. Additionally while a non-flexible catheter may be used without departing from the scope of the present invention, the use of flexible tubing beneficially provides for easier insertion and a reduction in potential tissue damage. Because there are currently apparatus available that can provide the correct amounts of an embryo solution, the hub of the device may be configured to attach to such apparatus. Alternatively, the catheter and the apparatus providing the embryo solution may be configured as an integral unit.

In practice, the device can be inserted through the cervix where embryos can then be expunged. Afterwards, the device can be removed. Accordingly, one of ordinary skill will appreciate that all three steps can be performed in non-anesthetized female animals. The lack of anesthesia provides a number of benefits over current surgical techniques for embryo transfers. These existing methodologies for embryo transfer in small rodents require the surgical transfer into anesthetized females. Anesthetics are considered to be "controlled substances" under DEA guidelines, which require specialized handling and storage.

As mentioned, embryo transfer using embodiments of the present invention eliminates the need not only for anesthesia but also for surgery. All current methods of embryo transfer in small rodents require surgical transfer. The surgical methods in small rodents are technically challenging and require substantial training and a high level of skill. Surgical transfer requires that females be anesthetized, as described above, and complications (mistakes during surgery, inappropriate levels of anesthesia, post operative infection) can lead to death of female mice. Surgery also leads to post-operative care of female mice. This care requires monitoring of the mice at regular intervals for several weeks post-surgery to insure that they are healthy and not suffering any complications (including infections) and the possible use of analgesics. Animal use guidelines also require that surgical instruments are sterile prior to use; sterilization requires autoclaves, which are expensive and shorten the usable life of costly high-precision surgical instruments.

An additional benefit of practicing the present invention is that it results in a dramatic time savings; surgical transfer require about 30 to 45 minutes of labor for each animal whereas use of embodiments of the present invention allows the transfer to be accomplished in less than one minute.

The use of genetically modified mice is well established as a critical aspect of biomedical research, and the use of such mice is expected to rise. At the same time, animal research in academic and private institutions is strictly regulated to insure proper treatment of animals, and guidelines for animal use continue to increase. Academic institutions are required to have IACUC (Institutional Animal Care and Use Committees) oversight to insure proper and humane use of animals. While it is acknowledged that animal research is an essential component of biomedical research, the use of animals is guided by "the three R's". These include replacement (using non-animal alternatives), reduction (the use of fewer animals to produce the desired result) and refinement (to reduce the incidence or severity of inhumane or painful procedures). Embodiments of the present invention completely eliminate the need for surgery while performing embryo transfer and provide an alternative, non-surgical transfer that is a much more humane, much less painful method.

FIG. 1 depicts a device 100 configured in accordance with the principles of the present invention. There is a hub portion that has a first end 102 and a second end 104. Extending from the second end 104 is a catheter 106 the terminates at a distal tip 108. The length 112 of the catheter 106 is discussed in detail below. The hub portion includes a cavity 110 that is in fluid communication with the inside passageway of the catheter 106. In this way, fluid or other material may be drawn into, and expelled from, the catheter tip 108 by application of the appropriate pressure at the cavity 110.

The first end 102 of the hub portion may be configured to be coupled with a pipeter or similar device that can be used to supply material into the cavity 110. The design of the first end 102 of the hub portion is not as critical; it is designed so that the hub portion may fit snugly on a pipeter such as, for example, a Gilson PIPETMAN® pipeter. However, other pipeters are available, and designing the first end 102 for use with other pipeters is contemplated within the scope of the present invention.

Figure 4:
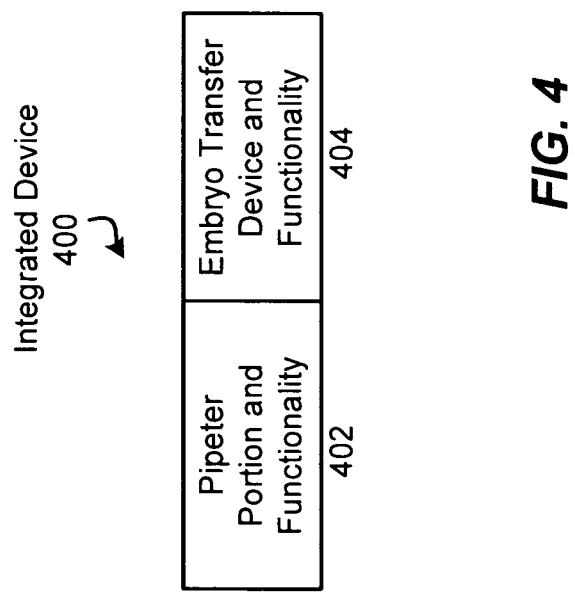
FIG. 4 depicts another embodiment of a non-surgical embryo transfer device in accordance with the principles of the present invention.

In addition to a pipeter, one of ordinary skill will recognize that there are a number of functionally equivalent devices for delivering an embryo solution that can be used instead of the pipeter without departing from the scope of the present invention. In yet another alternative shown in FIG. 4, a separate pipeter, or similar, device is not used. Rather, a single device 400, having an integrated pipeter 402 and transfer device 404, is used to carry out the entire procedure of loading and dispensing the embryo-containing solution, negating the need for a separate pipeter.

It is beneficial that the tip 108 is tapered in order to get through the cervix. The degree of the taper may be modified for devices depending on the type of animals on which they are used. As for manufacturing and material, the catheter 106 and tip 108 may be extruded from fluorinated ethylene propylene or FEP (TEFLON®) while the hub portion may be made from polyethylene, or the like. This selection of material advantageously provides a tip 108 that has rigidity but also some flexibility.

In FIG. 2, the catheter 106 is shown in relation to a speculum 202. In operation, the tip 108 of the catheter 106 extends into a proximate end 206 of the speculum 202 and exits out a distal end 204. In relation to being inserted in an animal, the distal end 204 may also be called the "front" end of the speculum 202. The speculum, which is inserted in the vagina of the animal, can be constructed of any semi-rigid plastic or composite material suitable for the intended environment. It can be constructed so as to be a disposable item or, alternatively, have a robust enough construction to allow sterilization and re-use. Furthermore, the speculum can be initially configured to be attached to the device prior to use or it can be, as mentioned above, a separate piece.

As shown, the device has a passageway within the hub and catheter that allows a solution received at the tip of the catheter to be drawn up into the catheter. In this way, the pipette and the device can deliver a embryo solution within an animal's uterus when the device is inserted through the cervix of that animal.

One beneficial aspect of the device 100 of FIG. 3 is the distance 310 from the end of the tip 108 to the front end 204 of the speculum 202. The device is sized such that when the speculum 202 is placed in the mammal's vagina 302, the distance 310 is sufficiently long to get past the cervix 304 and transfer the embryos into the uterus 306, but not so long as to extend far enough to damage the uterine wall 308. Thus, the back end 206 of the speculum 202 acts as a positive stop preventing the tip 108 from extending so far into the uterus as to cause damage. The flexibility of the tip 108 also helps prevent damage even if the uterine wall 308 is contacted.

One example mammal that the device can be used with is CD-1 mice. Because of slight physiological differences between different strains of mice, the distance 310 of the device 100 may vary slightly for different mouse strains. The distance 310 can be determined by performing testing on euthanatized female mice of different strains. In addition to CD-1 mice, the device can also be used for transcervical transfer of embryos in rats, other types of mice, and other mammals. Accordingly, because of the size difference between mice, rats and other mammals, a device 100 that is appropriate for each such animal will have its own, respective distance 310 that will differ among such devices.

By way of example, for CD-1 mice, the device 100 of FIG. 1 may have the following dimensions. One of ordinary skill will recognize that such dimensions are provided as the best mode known for use with a CD-1 mouse; however, embodiments of the present invention are not limited to only these specific dimensions. As discussed herein, the device 100 is sized to accommodate different species of animals in such a way as to allow embryos to be transferred past the cervix but without causing damage to the uterine walls. The overall length of the device 100 may be between about 1.6 and 1.7 inches with the hub portion 102, 104 being about 0.625 inches in length. Thus, the distance 112 of the catheter portion 106 may be about 0.9 to 1.1 inches. As for diameter, the catheter 106 may have an inner diameter (ID) of about 0.018 to about 0.021 inches and an outer diameter (OD) of about 0.028 to about 0.031 inches. As shown, the tip 108 tapers towards its end and this tapered section may be about the last 0.05 inches of the tip 108. As mentioned, these specific dimensions may be varied for various animals, and for mice as well, without departing from the scope of the present invention.

Also, one other factor to consider when sizing the device 100 for different animals is that the size of the speculum will likely be different for different animals. By way of example, with CD-1 mice, there are two differently sized speculums that may be used with the device. A smaller speculum is used to help open the vagina of the mouse. The smaller speculum dimensions may be about 0.087 inches ID, 0.109 inches OD, and a length of about 0.475 inches. As discussed, the device 100 and the speculum are designed to assist in the correct depth placement of the catheter inside the uterus. In one example, the larger speculum is sized appropriately with dimensions of about 0.140 inches ID, about 0.162 inches OD, and a length of about 0.400 inches. As for material, the speculums can be made of polyethylene or polypropylene.

As discussed above, one particular use of the device 100 is for non-surgical transfer of embryos into female mice. However, other embodiments of the invention contemplate that the device may be used for the transfer of sperm (fresh and cryopreserved) or for the transfer of cryopreserved blastocysts as well as embryos that are obtained by in vitro fertilization.

In at least one embodiment, the device is packaged in a sterile packaging and is intended to be disposed after each use. The user of the device may benefit from using a magnifying device when drawing the embryos into the catheter, but such an accessory is not required to practice the present invention.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method for non-surgical transfer of a fluid into a rodent, comprising the steps of:

(a) inserting a speculum into the rodent's vagina, the speculum having a distal end and a proximate end, wherein the speculum is inserted such that the distal end of the speculum is oriented closer to the uterus of the rodent;

(b) inserting a transfer device into the speculum, the transfer device including a hub portion and a catheter portion, the hub portion having a first end and a second end, wherein the catheter portion is in fluid communication with the hub portion and terminates at a distal tip;

wherein the catheter portion of the transfer device contains the fluid at or near the distal tip of the catheter portion in step (b), and wherein the fluid comprises at least one embryo, wherein the distal tip of the catheter portion of the transfer device is extended through the cervix and into the uterus of the rodent in step (b); and wherein the catheter portion of the transfer device is inserted into the speculum in step (b) until the second end of the hub portion contacts the proximate end of the speculum such that the catheter portion is prevented from being further inserted into the speculum.

2. The method of claim 1, wherein the distal tip of the catheter portion extends past the distal end of the speculum a predetermined distance when the catheter portion is fully inserted into the speculum in step (b), the catheter portion being fully inserted into the speculum in step (b) when the second end of the hub portion of the transfer device contacts the proximate end of the speculum.

3. The method of claim 2, wherein the predetermined distance is long enough for the distal tip of the catheter portion to extend past the cervix but short enough to prevent the distal tip from damaging or extending past the uterus of the rodent.

4. The method of claim 2, wherein the predetermined distance is a distance determined empirically by testing in the rodent.

5. The method of claim 2, further comprising:

(e) testing the rodent to determine the predetermined distance, wherein step (e) is performed prior to step (b).

6. The method of claim 1, further comprising:

(c) transferring the fluid out of the catheter portion and into the rodent's uterus, wherein step (c) is performed after step (b).

7. The method of claim 1, further comprising the step of:

(d) coupling the hub portion of the transfer device to a pipette to draw the fluid into the catheter portion of the transfer device, wherein step (d) is performed prior to step (b).

8. The method of claim 1, wherein the catheter portion is flexible.

9. The method of claim 1, wherein the distal tip of the catheter portion is tapered.

10. The method of claim 1, wherein the rodent is a mouse.

11. The method of claim 1, wherein the distal tip of the catheter portion comprises fluorinated ethylene propylene.

12. The method of claim 1, wherein the preventing of the catheter portion from being further extended into the speculum in step (b) stops the distal tip of the catheter portion from being further extended into or past the uterus of the rodent.

13. The method of claim 1, wherein the length of the speculum from the proximate end to the distal end is between about 0.400 inches and about 0.475 inches.

14. The method of claim 1, wherein the rodent is a rat.

15. The method of claim 14, wherein the catheter portion of the transfer device has a length of between about 0.9 inches and about 1.1 inches.

16. The method of claim 14, wherein the catheter portion of the transfer device has an outer diameter of between about 0.028 inches and about 0.031 inches.

17. The method of claim 1, wherein the overall length of the transfer device is from about 1.6 inches to about 1.7 inches.

18. The method of claim 1, wherein the lengths of the catheter portion and the speculum are predetermined empirically by testing in the rodent prior to step (a).

19. The method of claim 1, wherein the hub portion of the transfer device is wider than the inner diameter of the speculum.

20. The method of claim 1, further comprising:
(f) inserting a smaller speculum into the vagina of the rodent,
wherein the smaller speculum inserted in step (f) is removed from the rodent prior to step (a), wherein the speculum inserted in step (a) is a larger speculum, and wherein the larger speculum has an outer diameter that is larger than the outer diameter of the smaller speculum.

21. A method for non-surgical transfer of a fluid into a rodent, comprising the steps of:
(a) inserting a speculum into the rodent's vagina, the speculum having a distal end and a proximate end, wherein the speculum is inserted such that the distal end of the speculum is oriented closer to the uterus of the rodent;
(b) inserting a transfer device into the speculum, the transfer device including a hub portion and a catheter portion, the hub portion having a first end and a second end, wherein the catheter portion is in fluid communication with the hub portion and terminates at a distal tip, and wherein the transfer device is inserted into the speculum in step (b) until the hub portion of the transfer device contacts the proximate end of the speculum;
(c) transferring the fluid out of the catheter portion and into the rodent's uterus, wherein the fluid contains at least one embryo;
wherein the distal tip of the catheter portion extends past the distal end of the speculum a predetermined distance when the hub portion of the transfer device contacts the proximate end of the speculum in step (b),
wherein the catheter portion of the transfer device and the speculum each have a predetermined length to position the distal tip of the catheter portion in the uterus of the rodent when the hub portion contacts the proximate end of the speculum in step (b), and wherein the distal tip of the catheter portion of the transfer device is extended through the cervix and into the uterus of the rodent in step (b), and
wherein at least part of the hub portion of the transfer device is wider than the inner diameter of the speculum, and wherein the catheter portion of the transfer device is prevented from being further inserted into the speculum when the hub portion contacts the proximate end of the speculum in step (b).

22. The method of claim 21, wherein the fluid is transferred out of the catheter portion and into the uterus of the rodent in step (c) while the hub portion is contacting the proximate end of the speculum.

23. The method of claim 21, further comprising:
(d) coupling the hub portion of the transfer device to a pipette; and
(e) drawing the fluid into the catheter portion of the transfer device by operation of the pipette;
wherein steps (d) and (e) are performed prior to step (b).

24. The method of claim 23, wherein the fluid is transferred out of the catheter portion and into the uterus of the rodent in step (c) by operation of the pipette.

25. A method for non-surgical transfer of a fluid into a rodent, comprising the steps of:
(a) inserting a speculum into the rodent's vagina, the speculum having a distal end and a proximate end, wherein the speculum is inserted such that the distal end of the speculum is oriented closer to the uterus of the rodent;
(b) inserting a transfer device into the speculum, the transfer device including a hub portion and a catheter portion, the hub portion having a first end and a second end, wherein the catheter portion is in fluid communication with the hub portion and terminates at a distal tip;
wherein the catheter portion of the transfer device contains the fluid at or near the distal tip of the catheter portion in step (b), and wherein the fluid comprises sperm,
wherein the distal tip of the catheter portion of the transfer device is extended through the cervix and into the uterus of the rodent in step (b); and
wherein the catheter portion of the transfer device is inserted into the speculum in step (b) until the second end of the hub portion contacts the proximate end of the speculum such that the catheter portion is prevented from being further inserted into the speculum.

* * * * *